United States Patent [19]

Brown et al.

[11] Patent Number: 5,665,891
[45] Date of Patent: Sep. 9, 1997

[54] OXIDATION OF KETONES

[75] Inventors: Scott William Brown, Wigan; Alexander Johnstone, South Wirral; William Ronald Sanderson, Warrington, all of United Kingdom

[73] Assignee: Solvay Interox Limited, Warrington, England

[21] Appl. No.: 513,904

[22] PCT Filed: Mar. 8, 1994

[86] PCT No.: PCT/GB94/00440

§ 371 Date: Oct. 12, 1995

§ 102(e) Date: Oct. 12, 1995

[87] PCT Pub. No.: WO94/21624

PCT Pub. Date: Sep. 29, 1994

[30] Foreign Application Priority Data

Mar. 13, 1993 [GB] United Kingdom ............... 9305223

[51] Int. Cl.$^6$ ............... C07C 407/00; C07D 313/04
[52] U.S. Cl. ............... 549/272; 549/273; 549/295; 562/2; 562/3
[58] Field of Search ............... 549/272; 562/2, 562/3

[56] References Cited

U.S. PATENT DOCUMENTS 4,171,313  10/1979  Mares et al. ............... 568/860

FOREIGN PATENT DOCUMENTS 2138719  1/1973  France .
1050846  12/1966  United Kingdom .

OTHER PUBLICATIONS

Chemical Abstracts, vol. 114, 185237w (1991).

*Primary Examiner*—Bernard Dentz
*Attorney, Agent, or Firm*—Larson and Taylor

[57] ABSTRACT

A process for the catalysed oxidation of ketones to esters or lactones with hydrogen peroxide in the presence of a carboxylic acid or anhydride is provided. The process employs gamma alumina as a heterogeneous catalyst. In certain preferred embodiments the catalyst also contains a tungsten-containing heteropolyacid. Preferably, the heteropolyacid contains phosphorus. In a related process, the catalyst accelerates the formation of percarboxylic acid solutions.

28 Claims, No Drawings

OXIDATION OF KETONES

This application is a 371 of PCT/GB/00440 filed Mar. 8, 1994.

This invention concerns a process for the oxidation of ketones. Specifically, this invention concerns a process for the oxidation of ketones to esters and to the oxidation of cyclic ketones to lactones.

The oxidation of ketones to produce esters, and particularly the oxidation of cyclic ketones to produce lactones can be effected by peroxygen compounds. One of the most important industrial applications of such oxidation of ketones is the oxidation of cyclohexanone to produce caprolactone, which is widely employed in the production of polymers and co-polymers.

A number of different methods have been proposed or have found industrial application for the production of lactones. One such method is to oxidise the ketone with peracetic acid as a reagent. This method, although capable of excellent conversions requires the handling of relatively large quantities of concentrated peracetic acid solutions with its attendant hazards, and often requires the construction of dedicated plant for the production of the peracetic acid consumed in the oxidation process.

An alternative oxidant that is sometimes desirable to employ in the oxidation of alcohols is an aqueous solution of hydrogen peroxide, because it is relatively cheap, easy to handle and is environmentally acceptable in that its decomposition products are water and oxygen. In order to achieve effective oxidations of ketones with hydrogen peroxide, it has often been found necessary to employ a catalyst. Such catalysts are commonly employed as homogeneous catalysts i.e. they are employed in the same phase and/or physical state as the reagents. Although the use of homogeneous catalysts commonly has the advantage of a relatively high rate of reaction compared to other forms of catalyst, one drawback of such an approach is that the reaction depends on the formation of a solution of the catalyst, which is then brought into contact with the alcohol. This means that on completion of the reaction, the catalyst often remains in solution. Such a solution can, in theory, be separated from the reaction product and recycled, but in many cases, particularly where the product is a liquid, this process can involve a distillation stage. It is widely recognised that the distillation of a solution which may contain peroxide residuals is a potentially hazardous operation because the potential concentration of peroxides can result in the formation of explosive compositions. In order to mitigate against such hazards, solutions which may contain peroxide residuals are often chemically treated, typically with a reducing agent such as sodium metabisulphite solution, to remove any peroxide residuals. Unfortunately, such a chemical treatment can alter the chemical nature of catalyst remaining in solution, and this can mean that the activity of the catalyst is lost or significantly reduced when the solution is recycled, thereby rendering the recycling ineffective.

An alternative to recycling is to dispose of such solutions to waste, but such disposal is becoming increasingly regulated and correspondingly more expensive. In addition, such a disposal also represents a significant chemical cost because of the loss of chemicals, and particularly for relatively expensive catalysts. It has therefore become expedient to recover spent catalyst if possible, notwithstanding the problems outlined hereinbefore, but where the catalyst is in solution, such recovery can involve the construction and operation of relatively expensive separation plants.

An example of a method employing a homogeneous catalyst is that proposed in U.S. Pat. No. 4,160,769 to Union Carbide Corp. in which cyclohexanone is oxidised by hydrogen peroxide in the presence of selenium dioxide catalyst, the catalysis it is believed proceeding via the formation of soluble perselenic acid. This process suffers from the drawback that selenium compounds are highly toxic, and therefore care must be exercised in the handling of the catalyst, and in the removal of traces of the catalyst from any process effluent.

In order to facilitate or improve recovery and/or recycling of the catalyst and also allow relatively easy control of catalyst concentrations in plant effluent streams, one approach that can be contemplated is to employ a heterogeneous catalyst. As the majority of reaction systems employed are liquid, such heterogeneous catalysts are most commonly solids. However, if a catalyst is present in a different physical form to the reagents, the amount of intimate contact between them is reduced, and this can result in the rate of reaction being unacceptably low, or even in there being no reaction. This is illustrated by the method is disclosed in U.S. Pat. No. 4,870,192 to Mobil Oil Corp. in which cyclohexanone is oxidised by hydrogen peroxide in the presence of a zeolite catalyst such as ZSM-5. Although good selectivity is achieved, the conversion of cyclohexanone is in the order of only 5.6%, which is too low for an economic process. It is therefore desirable that the heterogeneous catalyst employed does not result in an unacceptably slow reaction.

Accordingly, it is an object of the present invention to provide a process for the oxidation of ketones to esters that involves reagents that are less hazardous and/or toxic than certain processes in the prior art.

It is a further objective of certain embodiments of the present invention to provide a process for the oxidation of ketones to esters in the presence of a heterogeneous catalyst that produces greater conversions of cyclohexanone than other processes in the prior art.

According to the present invention, there is provided a process for the oxidation of ketones comprising the reaction of a ketone with hydrogen peroxide in the presence of a solvent and employing a heterogeneous catalyst, characterised in that solvent comprises a carboxylic acid or anhydride and the catalyst comprises gamma alumina.

According to another aspect of the present invention, there is provided a catalysed process for the production of a percarboxylic acid by reaction between a carboxylic acid or anhydride and hydrogen peroxide, characterised in that the catalyst comprises gamma alumina.

According to a further aspect of the present invention, there is provided a catalysed process for the in situ generation of a percarboxylic acid by reaction between a carboxylic acid or anhydride and hydrogen peroxide, characterised in that the catalyst comprises gamma alumina.

In the process according to the present invention, the catalyst comprises gamma alumina. Gamma alumina can conveniently be prepared by calcining normal alumina or aluminium hydroxide at a temperature of about 300° C. to about 600° C. The gamma alumina is usually employed in the form of discrete particles, the particle size range often being selected such that the catalyst particles are distributed through the reaction mixture to a substantial extent during the agitation of the mixture. A convenient average particle size often lies in the range of from about 100 microns to about 5 mm.

The catalysts which can be employed in the process according to the present invention in some embodiments comprise gamma alumina alone. However, in other embodiments, gamma alumina comprises only part of the catalyst. Where this is the case, the percentage by weight of gamma alumina is often less than about 99%, preferably from about 70% to about 96%, and most preferably from about 95% to about 83%. The active catalyst can be diluted with one or more other components that have exhibited no or little catalytic activity themselves in the oxidation of ketones to lactones with hydrogen peroxide, such as normal or alpha alumina, other inorganic oxides such as silica, titanium dioxide, zirconia or magnesia, or organic resins, such as strong base ion exchange resins.

In certain particularly preferred embodiments, the active gamma alumina can be employed in conjunction with a second active catalyst species having at least some, and preferably significant, catalytic activity in the oxidation of ketones to lactones with hydrogen peroxide. Examples of such a second catalyst include particularly transition metal-containing heteropolyacids containing a non-metallic heteroatom which may be selected from Group IV including silicon and germanium or Group V including phosphorus. Preferably, the heteropolyacid contains phosphorus as the non-metallic heteroatom.

Tungsten or molybdenum, preferably tungsten, may constitute the entire metallic component of the heteropolyacid. Two transition metals, such as tungsten and molybdenum may be incorporated therein. Many heteropolyacids for employment in the present invention process can be represented by the empirical formula $M_{3/n}PW_wMo_{12-w}O_{40}$ when they are brought into contact with the gamma alumina in which w represents 0 or an integer of at least 1, preferably at least 6. Most preferably w represents 12. M represents hydrogen or other counterion, and n is its basicity in the general formula. It is believed that the catalyst retains its empirical ratio of tungsten to phosphorous and molybdenum, but that the interaction of the catalyst with the surface of the gamma alumina may result in the catalyst becoming bonded chemically to the gamma alumina, thereby modifying both the catalyst itself and the gamma alumina surface. Such treatments may also encourage a redistribution of the metal between species of different nuclearity.

Other heteropolyacids contemplated for use in the present invention include those containing at least one first series transition metal, including specifically iron, manganese, cobalt and nickel, for example in heteropolyacids of the formula $M_{(7-vy)/n}PW_{11}MxO_{36+v}$ in which Mx represents the other transition metal, v is its oxidation state and M is the counterion of basicity n as before.

It will be recognised that it is possible for the gamma alumina and the second catalyst to be simply a physical mixture without formal chemical bonding, and also that it is possible to add gamma alumina and any second catalyst to the reaction mixture separately. However, in certain preferred embodiments, the gamma alumina is chemically bonded to the second catalyst. The second catalyst often comprises from about 5% to about 15% of the active catalyst.

Second catalysts comprising heteropolyacids can be chemically bonded to the gamma alumina most conveniently by impregnation in solution in a suitable solvent, which can comprise water or a polar organic solvent such as a low molecular weight aliphatic alcohol or a mixture thereof. Low molecular weight herein indicates up to C4 (butanols). The solution can, in principle, contain any concentration of heteropolyacid up to and including a saturated solution, and in preference is at or near saturation, so as to minimise the volume of solvent that is subsequently removed. The solution can be contacted with the gamma alumina in bulk until a desired amount has been absorbed and after separation from the liquid phase, the impregnated gamma alumina is thereafter dried. The impregnation contact period often lasts from about 30 minutes to 8 hours. In a variation, the gamma alumina may be charged into a column through which a solution of the heteropolyacid is permitted to percolate, preferably with recycle of the eluate to maximise uptake of the heteropolyacid from the solvent.

The contact may be made at or around ambient temperature, which is typically in the region of from about 15° to 25° C. or it may be conducted at an elevated temperature up to the boiling point of the solvent under the selected pressure conditions. By employing an elevated temperature, and particularly one that is within 10° C. of the solvent boiling point, the solvent is evaporated away to at least some extent during the contact period. Once the solution has reached saturation, any further solvent removal results in the heteropolyacid being deposited on the gamma alumina. Accordingly, the gamma alumina can thereby be loaded with a higher level of heteropolyacid than is obtainable by simply impregnating the gamma alumina with a saturated solution, separating the gamma alumina from excess liquor and drying. Particularly for use in conjunction with solvent evaporation during the contact phase, the solvent is methanol or an alternative low boiling point solvent. It will be recognised that heteropolyacids can be impregnated onto other aluminas than gamma alumina, and which can then be calcined to form gamma alumina.

Where gamma alumina itself has been impregnated with heteropolyacid, it is not essential to calcine the post-impregnation material. However, it is preferred to calcine such material because during calcination, it is believed that formation of a bond between the heteropolyacid and the gamma alumina is promoted, which can assist in controlling the leaching of the heteropolyacid into the reaction mixture. It is advantageous to calcine at a temperature of at least 300° C. and usually not higher than about 600° C. In a number of instances, a particularly suitable temperature for calcination is at least about 400° C. and especially from about 450° to about 550° C.

The ketones that can be oxidised by the process according to the present invention can be aliphatic or aromatic, and may be linear, branched or cyclic. In many embodiments, the ketones will comprise less than about 20 carbon atoms, usually less than about 15 carbon atoms. Where the ketone is cyclic, the cyclic ring will usually comprises less than 12 carbon atoms, and will most often comprise from 4 to 8 carbon atoms. Examples of such cyclic ketones include cyclobutanone, cyclopentanone, cyclohexanone and cycloheptanone.

The solvent in the process according to the present invention comprises a carboxylic acid or carboxylic anhydride. Usually, the acid or anhydride will contain from 1 to about 6 carbon atoms, and suitable examples include acetic anhydride, acetic acid and propionic acid. The most preferred solvent is acetic acid.

The process according to the present invention is usually carried out at elevated temperature, typically from 50° C. up to the reflux temperature of the reaction medium, and particularly from about 60° to about 85° C. Particularly for substrates which boil under standard atmospheric pressure at lower temperatures than the desired reaction temperature, the reaction may be conducted at an elevated pressure selected so as to permit the desired temperature to be attained, but of course the higher boiling substrates may likewise be reacted at elevated pressure if desired.

It will be recognised that when dealing with relatively reactive and acid sensitive products such as esters, and particularly lactones, that, although it is possible to employ a stoichiometric or greater than stoichiometric mole ratio of hydrogen peroxide to ketone, it is often desirable to employ a substoichiometric mole ratio such as 0.5 mole of hydrogen peroxide per mole of substrate if the latter contains a single ketone group in order to reduce the amount of further reaction of the product with hydrogen peroxide. In many instances, a mole ratio of from 0.4:1 to about 0.8:1 hydrogen peroxide to ketone substrate is employed.

The hydrogen peroxide is preferably introduced into the reaction mixture in the form of a concentrated aqueous solution, and frequently of from about 35 to 70% w/w hydrogen peroxide. Preferably, the hydrogen peroxide is introduced into the reaction mixture which contains both the substrate and catalyst system, and particularly preferably it is introduced gradually, for example over a period of from 15 minutes to 4 hours. It will be recognised that in certain embodiments, all of the substrate is present in the reaction mixture prior to the commencement of the hydrogen peroxide addition. However, in other embodiments, it is preferred for there to be concurrent additions of ketone and hydrogen peroxide to the reaction mixture. When concurrent additions of ketone and hydrogen peroxide are employed, it is preferred for the additions to be separate to reduce the hazards associated with mixtures having a relatively high ratio of hydrogen peroxide to organics.

The ratio of gamma alumina catalyst to ketone substrate can be selected over a wide range of weight ratios, often in the range of from 1:1 to 1:50 and in a number of instances from 1:5 to 1:25. The ratio chosen can take into account the amount of other components on the gamma alumina catalyst and the activity of the substrate, as well as the other reaction conditions selected.

The volume of reaction medium employed is often selected in the range of from 1 to 15 volumes of solvent per volume of ketone substrate and in many instances within the range of from 2 to 10 volumes of solvent per volume of substrate.

The overall reaction period, including the period of introduction of the second reagent which is normally hydrogen peroxide, often comprises from about 2 to about 12 hours, and in many instances is from about 3 to about 8 hours. However, longer reaction periods of for example 12 to 30 hours can be employed, if desired by the user.

When the oxidation process has been permitted to continue for the desired period, the reaction can be halted by physically separating the particulate catalyst from the reaction mixture by filtration or centrifugation and/or by cooling the mixture for example to ambient. The recovered catalyst can be re-employed in a further reaction mixture, possibly after washing with solvent and/or drying and/or re-calcination, if desired.

It will be recognised that the foregoing description of the process variables has been directed primarily to the overall reaction involving the ketone substrate. Where the reaction is intended to generate a percarboxylic acid as the product, corresponding process conditions, such as reaction temperature can be employed. Likewise, the ratio of catalyst to carboxylic acid and of hydrogen peroxide to carboxylic acid can be varied within the ranges implicit in the foregoing disclosures.

In the percarboxylic acid composition aspect, it is particularly convenient to employ formic, acetic or propionic acid. At the discretion of the user, in this aspect of the invention, the weight ratio of catalyst to carboxylic acid is often selected in the range of from 1:200 to 1:1 and in many instances from 1:100 to 1:10. The mole ratio of hydrogen peroxide to carboxylic acid can be selected within a very wide range, and often depends on the composition of the product sought, since the catalyst accelerates the preparation towards on equilibrium composition. The mole ratio is often selected in the range of 10:1 to 1:10 for composition formation, though ratios outside that range can be contemplated for other equilibrium compositions. The reaction period for the percarboxylic acid composition preparation is under the control of the user. It will vary depending on the other process conditions, including in particular the reaction temperature and the proportion of catalyst in the mixture. In general, the reaction is normally permitted to continue for at least 30 minutes, but if ambient temperatures are employed a period of up to at least 7 days can be contemplated. In many instances the period is chosen in the range of 2 to 30 hours. In mixing especially the more concentrated aqueous hydrogen peroxide solutions such as from 50 to 70% w/w with the carboxylic acid, it is desirable to select the final weight proportions of the organic, hydrogen peroxide and water components of the composition such that the compositions are non-detonable and to so arrange the order of addition, such as by simultaneous introduction into a reservoir of both reactants or of progressive introduction of the hydrogen peroxide into the carboxylic acid that the instantaneous compositions are non-detonable.

The use of a solid, separable catalyst enables the peracid composition to be prepared quickly, and subsequent removal catalyst, eg by filtration, minimises the rate of any subsequent equilibration or re-equilibration.

For in situ generation of a percarboxylic acid for subsequent use, the mole ratio of carboxylic acid to hydrogen peroxide is desirably within the ranges derivable from the description given hereinbefore for the solvent: hydrogen peroxide, and is usually a substoichiometric amount of hydrogen peroxide.

Having described the invention in general terms, specific embodiments thereof are described in greater detail by way of example only.

Catalyst Preparation

The catalyst employed in Example 1 comprised gamma alumina alone which was commercially available in the UK from BDH Limited.

The catalyst employed in Examples 1, 5, 6 and 7 comprised gamma alumina loaded with a selected heteropolyacid which was obtained by the following general method. 3 g of the selected heteropolyacid was dissolved in 25 ml of demineralised water. To this solution was added 20 g of gamma alumina, and the mixture stirred at room temperature for 4 hours. The slurry was filtered, and the residue dried in an oven at 60° C. overnight. The dried solid was then calcined at 500° C. for 4 hours in a muffle furnace. The catalysts produced had a nominal heteropolyacid loading of 10% by weight.

The catalyst employed in Comparison 8 was prepared by the same general method as for Examples 1, 5, 6 and 7, except that alumina-free $TiO_2$ was employed in place of gamma alumina.

EXAMPLE 1

Cyclohexanone (5 g, 53 mmol), acetic acid (40 ml) and gamma $Al_2O_3$ (0.5 g) were charged to a reaction vessel and heated to 70° C. with stirring. Aqueous 35% w/w $H_2O_2$ (2.6 g, 26.5 mmol) was added over 20 minutes whilst maintaining stirring with the temperature maintained at 70° C. On completion of the $H_2O_2$ addition, reaction was continued for a further 6 hours. The reaction mixture was analysed hourly by gas chromatography. The results reported are for the analysis which gave the highest yield of product, as calculated from the conversion and selectivity figures.

After 6 hours, 41% of the cyclohexanone was converted, with a selectivity to caprolactone of 43%.

Comparison 2

The procedure of Example 1 was repeated, except that no catalyst was employed.

After 5 hours, 37% of the cyclohexanone was converted, with a selectivity to caprolactone of only 29%.

Comparison 3

The procedure of Example 1 was followed, except that alpha alumina (0.5 g) was employed as catalyst.

After 6 hours, 60.3% of the cyclohexanone was converted, with a selectivity to caprolactone of only 13.2%.

Comparison 4

The procedure of Example 1 was followed, except that 60–120 mesh silica (0.5 g) was employed as catalyst.

After 5 hours, 30.7% of the cyclohexanone was converted, with a selectivity to caprolactone of only 22.7%.

EXAMPLE 5

The procedure of Example 1 was followed except that 0.5 g of $H_3PW_{12}O_{40}$ chemically bonded to gamma alumina with a nominal loading of 10% was employed as catalyst.

After 4 hours, 38% of the cyclohexanone was converted, with a selectivity to caprolactone of 85%.

EXAMPLE 6

The procedure of Example 1 was followed except that 0.5 g of $H_4SiW_{12}O_{40}$ chemically bonded to gamma $Al_2O_3$ was employed as catalyst.

42% of the cyclohexanone was converted, with a selectivity to caprolactone of 46%.

EXAMPLE 7

In this Example, cyclohexanone (5 g, 53 mmol), acetic acid (40 ml) and $H_3PW_{12}O_{40}$ chemically bonded to gamma $Al_2O_3$ (0.5 g) were charged to a reaction vessel and heated to 80° C. with stirring. The reaction temperature and stirring were maintained throughout. Aqueous 35% w/w $H_2O_2$ (2.6 g, 26.5 mmol) was added over 20 minutes. 2 hours after the completion of the first $H_2O_2$ addition, a further aliquot of aqueous 35% w/w $H_2O_2$ (2.6 g, 26.5 mmol) was added over 20 minutes, and then the reaction continued for a further 1 hour.

60% of the cyclohexanone was converted, with a selectivity to caprolactone of 69%.

Comparison 8

The procedure of Example 1 was followed except that 0.5 g of $H_3PW_{12}O_{40}$ chemically bonded to titanium dioxide with a nominal heteropolyacid loading of 10% was employed as catalyst.

After 6 hours, 41.2% of the cyclohexanone was converted, with a selectivity to caprolactone of 34.2%.

Comparison 9

The procedure of Example 1 was repeated, except that $H_3PW_{12}O_{40}$ (0.5 g) was employed as a homogeneous catalyst.

After 5 hours, 60% of the cyclohexanone was converted, but no caprolactone was detected.

EXAMPLE 10

Acetic acid (47.2 g) and $H_3PW_{12}O_{40}$ chemically bonded to gamma alumina with a nominal loading of 10% (0.5 g) were charged to a reaction vessel and heated to 90° C. with stirring. Aqueous 70% w/w $H_2O_2$ (3.0 g, 61.7 mmol) and cyclohexanone (11.25 g, 114.8 mmol) were added separately and concurrently over 2 hours using peristaltic pumps whilst maintaining stirring with the temperature maintained at 90°C. On completion of the additions, reaction was continued for a further 2.2 hours. The reaction mixture was then analysed by gas chromatography.

The results showed that 40% of the cyclohexanone was converted, with a selectivity to caprolactone of 76%.

The result of Example 1 showed that gamma alumina increased the conversion of cyclohexanone and significantly increased the selectivity to caprolactone compared with the situation where no catalyst was employed, as illustrated in Comparison 2. Comparisons 3 and 4 demonstrated that this improvement was not obtained by the use of alpha alumina and silica respectively. The results of Examples 5 and 6 demonstrated that the employment of a second catalyst species loaded onto the gamma alumina improved the selectivity of caprolactone production, particularly where the heteroatom employed in the second catalyst is phosphorus. The result of Example 7 demonstrated that the use of 2 hydrogen peroxide additions increased the conversion of cyclohexanone whilst maintaining good selectivity to caprolactone. The result of Comparison 8 demonstrated that the use of a phosphorus-containing heteropolyacid catalyst loaded onto $TiO_2$ gave a lower conversion of cyclohexanone than where no catalyst was employed. The result of Comparison 9 demonstrated that the use of a homogenous heteropolyacid catalyst gave no detectable caprolactone. The result of Example 10 demonstrated that a concurrent addition of ketone and hydrogen peroxide could successfully be employed.

EXAMPLE 11 and Comparison 12

In Example 11, acetic acid (50 g) and a catalyst comprising $H_3PW_{12}O_{40}$ chemically bonded to gamma alumina with a nominal loading of 10% (1 g) were charged to a reaction vessel and heated to 70° C. with stirring. Aqueous 33.3% w/w $H_2O_2$ (5.95 g) was introduced progressively over 1 hours using a peristaltic pump whilst maintaining stirring with the temperature maintained at 70° C. On completion of the addition, the reaction was continued for a further 2 hour and 10 minutes. The reaction mixture was analysed for peracetic acid 10 minutes, 70 minutes and 130 minutes after completion of the addition of hydrogen peroxide. In Comparison 12, the procedure of Example 11 was employed, except that the catalyst was omitted. The results are given in Table 1 below.

TABLE 1

| | % w/w Peracetic acid | |
|---|---|---|
| Time (mins) | Example 11 | Comparison 12 |
| 10 | 2.2 | 1.2 |
| 70 | 4.1 | 2.6 |
| 130 | 4.9 | 3.5 |

The results in Table 1 clearly demonstrate the improved production of peracetic acid that can be achieved by the use of the process according to the present invention.

We claim:

1. In a process for the oxidation of ketones comprising the reaction of a ketone with hydrogen peroxide in the presence of a solvent and employing a heterogeneous catalyst, the improvement wherein the solvent comprises a carboxylic acid or anhydride and the catalyst comprises gamma alumina.

2. A process according to claim 1, characterized in that the catalyst additionally comprises a tungsten-containing heteropolyacid.

3. A process according to claim 2, characterized in that the heteropolyacid comprises a heteroatom selected from Group IV and Group V.

4. A process according to claim 3, characterized in that the heteroatom is phosphorus.

5. A process according to any of claims 1–4, characterized in that the tungsten containing heteropolyacid has the empirical formula $M_{3/n}PW_{12}O_{40}$ when brought into contact with the gamma alumina, in which M represents hydrogen or other counterion, and n is its basicity in the general formula.

6. In a process for the oxidation of ketones comprising the reaction of a ketone with hydrogen peroxide in the presence of a solvent and employing a heterogeneous catalyst, the improvement wherein the solvent comprises a carboxylic acid or anhydride and the catalyst comprises gamma alumina and a tungsten containing heteropolyacid having the empirical formula $M_{3/n}PW_{12}O_{40}$ when brought into contact with the gamma alumina, in which M represents hydrogen or other counterion, and n is its basicity in the general formula.

7. A process according to either of claims 1 or 6, characterized in that the carboxylic acid or anhydride solvent comprises from 1 to 6 carbon atoms.

8. A process to claim 7, characterized in that the solvent is acetic acid.

9. A process according to either of claims 1 or 6, characterized in that the oxidation is carried out at a temperature of from 50° C. to the reflux temperature of the reaction medium.

10. A process according to either of claims 1 or 6, characterized in that the hydrogen peroxide is employed at a mole ratio to ketone of from about stoichiometric to about 0.4:1.

11. A process according to claim 10, characterized in that the mole ratio of hydrogen peroxide to ketone is from 0.5:1 to 0.8:1.

12. A process according to either claims 1 or 6, characterized in that the weight ratio of catalyst to ketone is from 1:1 to about 1:50.

13. A process according to claim 12, characterized in that the weight ratio of catalyst to ketone is from about 1:5 to about 1:25.

14. A process according to either of claims 1 or 6, characterized in that the hydrogen peroxide solution employed has a concentration of from about 35% w/w to about 70% w/w.

15. A process according to either of claims 1 or 6, characterized in that the ketone comprises less than about 20 carbon atoms.

16. A process according to claim 15, characterized in that the ketone comprises a cyclic ketone.

17. A process according to claim 16, characterized in that the cyclic ketone comprises form 4 to 8 carbon atoms in its ring.

18. A process according to claim 17, characterized in that the ketone comprises cyclobutanone, cyclopentanone, cyclohexanone or cycloheptanone.

19. A process according to claim 1 or 6, characterized in that a concurrent addition of ketone and hydrogen peroxide solution is employed.

20. In a catalysed process for the production of a percarboxylic acid by reaction between a carboxylic acid or anhydride and hydrogen peroxide, the improvement wherein the catalyst comprises gamma alumina.

21. In a process for the in situ generation of percarboxylic acid by reaction between a carboxylic acid or anhydride and hydrogen peroxide in the presence of a catalyst, the improvement wherein the catalyst comprises gamma alumina.

22. A process according to claim 20 or 21, characterized in that the carboxylic acid or anhydride contains from 1 to 6 carbon atoms.

23. A process according to claim 22, characterized in that the carboxylic acid is acetic acid.

24. A process according to either of claims 20 or 21, further characterized in that the catalyst further comprises a tungsten-containing heteropolyacid.

25. A process according to either of claims 20 or 21, further characterized in that water is present in the reaction mixture corresponding to the amount corresponding to use of 35 to 70% w/w aqueous hydrogen peroxide solution.

26. A process according to claim 24 wherein the heteropolyacid comprises a heteroatom selected from Group IV and Group V.

27. A process according to claim 26 wherein the heteroatom is phosphorous.

28. A process according to claim 24, wherein the heteropolyacid has the empirical formula $M_{3/n}PW_{12}O_{40}$ when brought into contact with the gamma alumina, in which M represents hydrogen or other counterion, and n is its basicity in the general formula.

\* \* \* \* \*